United States Patent [19]

Van der Veken et al.

[11] 4,278,684

[45] Jul. 14, 1981

[54] NON-TOXIC ANTHELMINTHIC POUR-ON COMPOSITION

[75] Inventors: Guido J. L. Van der Veken, Turnhout; Jozef C. J. Dockx, Vosselaar, both of Belgium

[73] Assignee: Janssen Pharmaceutica N.V., Beerse, Belgium

[21] Appl. No.: 160,248

[22] Filed: Jun. 17, 1980

[51] Int. Cl.³ ............................................ A61K 31/425
[52] U.S. Cl. ................................................... 424/270
[58] Field of Search ................................. 424/270, 80

[56] References Cited

PUBLICATIONS

Andrews et al., Chem. Abst. vol. 88, (1978), p. 65976j.

*Primary Examiner*—Sam Rosen
*Attorney, Agent, or Firm*—Geoffrey G. Dellenbaugh

[57] ABSTRACT

The present invention relates to non-aggressive pour-on compositions for combating helminthic infestations in a non-human animal, said compositions comprising an anthelminthic amount of tetramisole and/or levamisole, a carboxylic acid and a di(lower alkyl) ester of a dicarboxylic acid.

19 Claims, No Drawings

NON-TOXIC ANTHELMINTHIC POUR-ON COMPOSITION

DESCRIPTION OF THE INVENTION

The method of systemically administering drugs by pouring or spraying a composition, comprising the desired drug, onto any part of the skin is generally known in veterinary medicine as the pour-on method. Drugs, administered following this method, are absorbed by the skin and, after they have penetrated through the skin, they are transmitted systemically within the animal. [see, for example, W. M. Rogoff and P. H. Kohler, J. Econ. Ent., 53, 814–817 (1960) and B. Idson, J. Pharm., Sci., 64, 901–924 (1975)]. In order to facilitate the penetration through the skin the drug is preferably applied in admixture with an appropriate carrier, which may be any liquid, taking up an adequate amount of the anthelminthic and permitting an adequate resorption of the drug through the skin without damaging the tissues. Said carrier may also consist of a mixture of vehicles, the resulting composition being a cream, a suspension or a solution.

In comparison with the parenteral administration methods the pour-on method offers distinct advantages. For example, there is no need to hold the animal, sterile precautions are not necessary and especially trained personal is not required.

In comparison with the oral administration methods, the pour-on method has the advantage that each animal receives an exactly defined amount of the desired drug.

Tetramisole, being chemically designated as 2,3,5,6-tetrahydro-6-phenylimidazo[2,1-b]thiazole and the laevo isomer thereof, levamisole, have been described in U.S. Pat. Nos. 3,274,209, respectively 3,463,786. The compounds are powerful anthelminthic agents. Structurally, tetramisole is represented by the formula

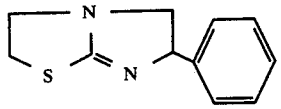
(I)

Anthelminthic pour-on compositions which contain tetramisole, levamisole or an acid-addition salt thereof, have been described in U.S. Pat. Nos. 4,070,476 and 3,980,791. Said compositions have the disadvantage that the carriers, which are the most effective for helping the penetration of the anthelminthic through the skin, are at the same time the most aggressive to the treated skin, resulting in, for example, subcutaneous bleedings, necrosis, hair and skin diseases and, at worst, open wounds. [severe skin irritations, caused by pour-on compositions, are described, e.g., in Veterinär Medizinische Nachrichten 1978 (1), 109–112].

The present invention describes new pour-on compositions for combating helminthic infestations in a non-human animal. In comparison with the art-known compositions the subject compositions are less aggressive and, due to their enhanced skin penetration, they are yielding higher plasma levels.

This invention relates to pour-on compositions for combating helminthic infestations in a non-human animal, which comprise:

a. an anthelminthically effective amount of dl-2,3,5,6-tetrahydro-6-phenylimidazo[2,1-b]thiazole and/or the laevo isomer thereof;

b. one or more optionally substituted aliphatic carboxylic acids, having each a pKa-value comprised between 3 and 6, the molar ratio of the total amount of said carboxylic acids to the total amount of the anthelminthics varying between 0.01 and 3; and c. an amount, varying from 10 to 70% by volume, of at least one di(lower alkyl) dicarboxylic acid ester of the formula

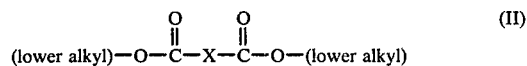
(II)

wherein X represents a direct bond or an alkylene radical having from 1 to 12 carbon atoms.

As used in the foregoing and in the following definitions all percentages refer to volumes; the pKa-value has the meaning of $-\log Ka$, wherein Ka is the dissociation constant of the most acidic function of the molecule at 25° C. in aqueous medium; the term "lower alkyl" is meant to include straight and branched hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; and "alkylene" comprises straight and branched alkylene chains.

Suitable optionally substituted aliphatic carboxylic acids are, for example, acetic acid, propionic acid, citric acid, lactic acid and the like. It is unexpectedly observed that in the subject compositions the said carboxylic acids act as specific skin penetration promotors.

Preferred compositions according to the present invention are those wherein the molar ratio of the total amount of the aliphatic carboxylic acids and the total amount of the anthelminthics varies between 0.05 and 1, said carboxylic acids having, more preferably, a pKa-value comprised between 4 and 5.5. Particularly preferred compositions are those wherein the aliphatic carboxylic acid is acetic acid.

Diesters of formula (II) wherein X is a lower alkylene radical having from 3 to 10 C-atoms are especially preferred and compositions containing 25 to 60% of such diesters are more especially preferred. Particularly preferred diesters of formula (II) are the di(lower alkyl) esters of adipic acid and the most preferred diesters of formula (II) are those wherein both lower alkyl radicals have 3 carbon atoms.

Since the anthelminthic activity of tetramisole is exerted essentially by the laevo isomer, in a preferred embodiment levamisole is employed as the anthelminthically active agent, and, in the most preferred embodiment the composition contains from 5 to 20 g. levamisole per 100 ml. of the resulting compositions.

Besides one or more anthelminthic agents, one or more diesters of formula (II) and one or more optionally substituted aliphatic carboxylic acids the compositions may also contain additives which may facilitate the administration to the skin of the animal and/or which may be helpful for preparing the desired compositions.

In order to reduce their viscosity, the compositions preferably comprise also from 10 to 60% of an aliphatic hydrocarbon mixture. Said aliphatic hydrocarbons, which reduce the surface tension of the compositions, prevent at the same time an excessive adhesion of the applied compositions to the hair and facilitate their spreading over the skin, resulting in an enhanced resorption of the anthelminthic by the skin. Useful hydrocarbon mixtures have, preferably, a boiling range comprised between 150° C. and 250° C. Particularly preferred hydrocarbon mixtures have a boiling range comprised between 170° C. and 230° C.

The presence of dipolar aprotic solvents, which act as a specific penetration promotors and skin protectants, may be advantageous. Suitable dipolar aprotic solvents are e.g., N,N-dimethylformamide, N,N-dimethylacetamide, dimethylsulfoxide, N-methyl-2-pyrrolidone and the like. Preferred compositions contain from 1 to 30% of a suitable hydrating agent. In the particularly preferred compositions said hydrating agent is N-methyl-2-pyrrolidone. The most preferred compositions contain from 5 to 15% of N-methyl-2-pyrrolidone.

In order to prepare compositions which are homogeneous, even at relatively low temperatures, it may be appropriate to add a co-solvent such as, for example, alcohols, e.g., 2-propanol and the like. Preferred compositions contain from 0 to 10% of a co-solvent and particularly preferred compositions contain from 0 to 5% of a co-solvent. The most preferred co-solvent is 2-propanol.

The compositions may also contain other additives such as, for example, substances whose taste deters animals from licking the applied compositions off the animals treated, pigments making it possible to recognize the treated animals and the like.

The above described compositions are especially characterized by their effectiveness and by their low ratio of irritation.

The effectiveness of the concerned anthelminthic pour-on compositions can be demonstrated by the amount of levamisole or tetramisole present in the blood plasma of the animal after treatment of said animal with one of the hereinabove described compositions.

THE EXPERIMENTAL DETERMINATION OF LEVAMISOLE AND/OR TETRAMISOLE IN BLOOD PLASMA

1. Sample preparation:

Venous blood samples are taken on a coagulating agent, e.g., heparine and the like, and, subsequently, they are mixed and centrifugated at 3000 rpm for 5 minutes, thus yielding a supernatant plasma.

2. Extraction procedure:

An aqueous solution, consisting of 2 ml. of the above described supernatant plasma, 100 μl. of a 10 ng/ml. solution of an internal standard, preferably (±)-2,3,5,6-tetrahydro-6-(4-methylphenyl)imidazo[2,1-b]thiazole hydrochloride, and 0.5 ml. of sodium hydroxide 10 N is extracted with 4 ml. of a hexane/ether (1/1) mixture. The organic layer is separated and extracted with 2 ml. of a 0.1 N sulfuric acid solution. Subsequently the aqueous layer is separated, washed with a hexane/ether mixture, alkalized with ammonia to pH 9 and extracted with trichloromethane. The trichloromethane layer is separated and the solvent is evaporated at 40° C. under a gentle stream of nitrogen. To the dry extraction sample there are added 50 μl. of pure methanol, thus yielding a sample which is suitable for gas chromatographic analysis.

3. Determination and calculations:

The amount of tetramisole and/or levamisole is determined by separating the components which are present in the hereinabove described sample following art-known gas chromatographic techniques and, subsequently, by comparing the peak area of levamisole and/or tetramisole with the peak area of the internal standard.

The levamisole and/or tetramisole plasma levels can be determined by the formula:

concentration of levamisole or tetramisole =

$$\frac{\text{peak area levamisole/tetramisole}}{\text{peak area internal standard}} \times F \times \text{concentration of internal standard}$$

wherein F is the response factor, which may be determined by the formula:

$$F = \frac{AI \times CR}{AR \times CI}$$

wherein AI, respectively AR, is the peak area of the internal standard, respectively of the reference compound, and wherein CR and CI are the concentration of the reference compound, respectively the internal standard.

The plasma-levels represented in tables 1, 2, 3 and 4 are intended to illustrate and not to limit the scope of the present invention.

Table 1 shows the concentrations of levamisole in the blood-plasma of cattle, which have received levamisole by pouring on the back of the animal a composition comprising:

10 g. levamisole;
10 ml. N-methyl-2-pyrrolidone;
35 ml. di(2-propyl) adipic acid ester;
5 ml. 2-propanol;
1 ml. acetic acid; and
Shellsol T ad 100 ml, wherein Shellsol T is an aliphatic hydrocarbon fraction having a boiling range comprised between 170° C. and 230° C.

Column 1 shows the average concentration of levamisole in the plasma of 12 cattle 0.5, 1, 2 and 4 hours after administration of 10 mg per kg of body weight and column 2 shows the average concentrations after administering 4 mg per kg of body weight to 4 cattle.

TABLE 1

| | μg. levamisole/ml blood plasma | |
|---|---|---|
| time after treatment in hours | administered dose = 10 mg/kg body weight | administered dose = 4 mg/kg body weight |
| 0.5 | 0.73 | 0.29 |
| 1 | 1.44 | 0.48 |
| 2 | 1.14 | 0.40 |
| 4 | 0.48 | 0.19 |

Table 2 shows the average concentrations of levamisole in the bloodplasma of 3 cattle after treatment with 10 mg of levamisole per kg of body weight by pouring on the back of the animal a composition comprising:

10 g. levamisole;
10 ml. N-methyl-2-pyrrolidone;
35 ml. di(2-propyl) adipic acid ester;
5 ml. 2-propanol;
0.5 ml. acetic acid (column a) or
3 ml. acetic acid (column b); and
Shellsol T ad 100 ml.

TABLE 2

| time after treatment in hours | μg. levamisole/ml blood plasma administered dose = 10 mg/kg body weight | |
|---|---|---|
| | 0.5% acetic acid | 3% acetic acid |
| 0.5 | 0.97 | 0.74 |
| 1 | 1.83 | 1.76 |
| 2 | 0.97 | 1.17 |
| 4 | 0.58 | 0.50 |

Table 3 shows the average concentrations of levamisole in the blood-plasma of 2 cattle after treatment with 10 mg of levamisole per kg of body weight by pouring on the back of the animal a composition comprising:
10 g. levamisole;
10 ml. N-methyl-2-pyrrolidone;
35 ml. dibutyl sebacic acid ester;
5 ml. 2-propanol;
1 ml.acetic acid; and
Shellsol T ad 100 ml.

TABLE 3

| time after treatment in hours | μg. levamisole/ml blood plasma administered dose = 10 mg/kg body weight |
|---|---|
| 0.5 | 0.72 |
| 1 | 1.17 |
| 2 | 0.95 |
| 4 | 0.27 |

Table 4 shows the concentration of levamisole in the bloodplasma of a sheep after treatment with 20 mg of levamisole per kg of body weight by pouring on the back of the animal a composition comprising:
10 g. levamisole;
10 ml. N-methyl-2-pyrrolidone;
35 ml. di(2-propyl) adipic acid ester;
5 ml. 2-propanol;
1 ml. acetic acid; and
Shellsol T ad 100 ml., (column a).
and by pouring on the back of the animal a composition comprising:
10 g. levamisole;
10 ml. N-methyl-2-pyrrolidone;
35 ml. dibutyl sebacic acid ester;
5 ml. 2-propanol;
1 ml. acetic acid; and
Shellsol T ad 100 ml. (column b).

TABLE 4

| time after treatment in hours | μg. levamisole/ml blood plasma administered dose = 20 mg/kg body weight | |
|---|---|---|
| | column a | column b |
| 0.5 | 0.35 | 0.29 |
| 1 | 0.40 | 0.30 |
| 2 | 0.79 | 0.39 |
| 4 | 0.48 | 1.02 |

The hereinabove described compositions can be prepared in a conventional manner, e.g., by adding the desired amounts of levamisole and/or tetramisole to a well-stirred mixture consisting of suitable amounts of the optionally substituted aliphatic carboxylic acids, the di(lower alkyl) carboxylic acid esters of formula (II), the co-solvent and the hydrating agents, and, subsequently, diluting the thus obtained mixture with an appropriate aliphatic hydrocarbon fraction.

Although the hereinabove described compositions are useful for combating helminthic infestations in all non-human animals, said compositions are especially preferred for the treatment of cattle and sheep.

The following examples are intended to illustrate and not to limit the scope of the present invention.

EXAMPLE 1

Over a period of 20 minutes, 10 grams of levamisole are added to a well-stirred mixture, consisting of
10 ml. anhydric N-methyl-2-pyrrolidone;
35 ml. diisopropyl adipate;
5 ml. 2-propanol; and
1 ml. acetic acid.
After completion, the whole is diluted to 100 ml. with Shellsol T.

EXAMPLE 2

Following the procedure described in Example 1 the following compositions are prepared:
composition 1:
10 g. levamisole;
10 ml. N-methyl-2-pyrrolidone;
35 ml. di(2-propyl) adipic acid ester;
5 ml. 2-propanol;
1 ml. acetic acid;
Shellsol T ad 100 ml.
Composition 2:
10 g. levamisole;
10 ml N-methyl-2-pyrrolidone;
35 ml di(2-propyl) adipic acid ester;
5 ml 2-propanol;
0.5 ml acetic acid;
Shellsol T ad 100 ml.
composition 3:
10 g. levamisole;
10 ml N-methyl-2-pyrrolidone;
35 ml di(2-propyl) adipic acid ester;
5 ml 2-propanol;
3 ml acetic acid;
Shellsol T ad 100 ml.
composition 4:
10 g. levamisole;
10 ml N-methyl-2-pyrrolidone;
35 ml dibutyl sebacic acid ester;
5 ml 2-propanol;
1 ml acetic acid;
Shellsol T ad 100 ml.

What is claimed is:

1. A pour-on composition for combating helminthic infestations in a non-human animal, comprising:
   a. an anthelminthically effective amount of dl-2,3,5,6-tetrahydro-6-phenylimidazo[2,1-b]thiazole and/or the laevo isomer thereof;
   b. one or more aliphatic carboxylic acids, having each a pKa-value between 3 and 6, the molar ratio of the total amount of said carboxylic acids to the total amount of the anthelminthics varying between 0.01 and 3; and
   c. an amount, varying from 10 to 70% by volume, of at least one di(lower alkyl) dicarboxylic acid ester of the formula

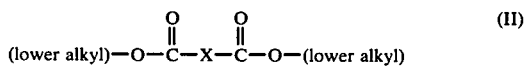

$$\text{(lower alkyl)}-O-\overset{O}{\underset{\|}{C}}-X-\overset{O}{\underset{\|}{C}}-O-\text{(lower alkyl)} \qquad (II)$$

wherein X represents a direct bond or an alkylene radical having from 1 to 12 carbon atoms.

2. A pour-on composition according to claim 1, containing additionally from 1 to 30% of a dipolar aprotic solvent.

3. A pour-on composition according to claim 2, containing additionally from 10 to 60% of an aliphatic hydrocarbon fraction having a boiling range between 150° C. and 250° C.

4. A pour-on composition according to claim 3, wherein the aliphatic hydrocarbon fraction has a boiling range between 170° C. and 230° C.

5. A pour-on composition according to claim 4, wherein the dipolar aprotic solvent is N-methyl-2-pyrrolidone.

6. A pour-on composition for combating helminthic infestations in a non-human animal comprising:
 a. an anthelminthically effective amount of dl-2,3,5,6-tetrahydro-6-phenylimidazo[2,1-b]thiazole and/or the laevo isomer thereof;
 b. one or more aliphatic carboxylic acids, having each a pKa-value comprised between 3 and 6, the molar ratio of the total amount of said carboxylic acids to the total amount of the anthelminthics varying between 0.01 and 3;
 c. an amount, varying from 10 to 70% by volume, of the at least one di(lower alkyl) dicarboxylic acid ester of the formula

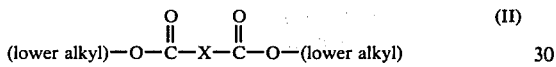
(II)

wherein X represents a direct bond or an alkylene radical having from 1 to 12 carbon atoms;
 d. an amount, varying from 5 to 15% of N-methyl-2-pyrrolidone; and
 e. an amount, varying from 10 to 60% of an aliphatic hydrocarbon fraction, having a boiling range between 170° C. and 230° C.

7. A pour-on composition according to claim 6, wherein X in the di(lower alkyl) dicarboxylic acid ester of formula (II) represents an alkylene radical having from 3 to 10 carbon atoms.

8. A pour-on composition according to claim 7, wherein the amount of di(lower alkyl) dicarboxylic acid ester of formula (II) varies between 25 and 60%.

9. A pour-on composition according to claim 8, wherein the di(lower alkyl) dicarboxylic acid ester of formula (II) is a di(lower alkyl) adipic acid ester.

10. A pour-on composition according to claim 9, wherein both lower alkyl radicals within the di(lower alkyl)adipic acid ester have 3 carbon atoms.

11. A pour-on composition according to claim 10, comprising additionally from 0 to 15% of a co-solvent.

12. A pour-on composition according to claim 10, comprising additionally from 0 to 5% of a co-solvent.

13. A pour-on composition according to claim 12, wherein the co-solvent is an alcohol.

14. A pour-on composition according to claim 13, wherein the co-solvent is 2-propanol.

15. A pour-on composition according to claim 14, wherein the ratio of the total amount of aliphatic carboxylic acids to the total amount of the anthelminthics varies between 0.05 and 1.

16. A pour-on composition according to claim 15, wherein the aliphatic carboxylic acids have pKa-values between 4 and 5.5.

17. A pour-on composition according to claim 16, wherein the aliphatic carboxylic acid is acetic acid.

18. A pour-on composition according to claim 17, wherein the anthelminthic is 1-2,3,5,6-tetrahydro-6-phenylimidazo[2,1-b]thiazole.

19. A pour-on composition for combating helminthic infestations in a non-human animal comprising:
 a. from 5 to 20 g. 1-2,3,5,6-tetrahydro-6-phenylimidazo[2,1-b]thiazole per 100 ml of the resulting composition;
 b. acetic acid, the molar ratio of the amount of acetic acid to the amount of 1-2,3,5,6-tetrahydro-6-phenylimidazo[2,1-b]thiazole varying between 0.05 and 1;
 c. an amount, varying from 25 to 60% by volume, of di(1-propyl)adipic acid ester and/or di(2-propyl)adipic acid ester;
 d. an amount, varying from 5 to 15%, of N-methyl-2-pyrrolidone;
 e. an amount, varying from 10 to 60%, of an aliphatic hydrocarbon fraction, having a boiling range between 170° C. and 230° C.; and
 f. an amount, varying from 0 to 5% of 2-propanol.

* * * * *